United States Patent
Sarhan

(10) Patent No.: US 10,966,659 B2
(45) Date of Patent: Apr. 6, 2021

(54) MULTIPLE SENSOR WEARABLE AND PORTABLE NON-INVASIVE RESPIRATION MONITORING INSTRUMENTATION

(71) Applicant: Sameh Sarhan, Santa Clara, CA (US)

(72) Inventor: Sameh Sarhan, Santa Clara, CA (US)

(73) Assignee: Xtrava, Inc., Santa Clara, CA (US)

( * ) Notice: Subject to any disclaimer, the term of this patent is extended or adjusted under 35 U.S.C. 154(b) by 0 days.

(21) Appl. No.: 16/257,034

(22) Filed: Jan. 24, 2019

(65) Prior Publication Data

US 2019/0254606 A1    Aug. 22, 2019

Related U.S. Application Data

(60) Provisional application No. 62/632,907, filed on Feb. 20, 2018.

(51) Int. Cl.
| | | |
|---|---|---|
| *A61B 5/053* | (2021.01) | |
| *A61B 5/00* | (2006.01) | |
| *A61B 5/0205* | (2006.01) | |
| *A61B 5/318* | (2021.01) | |
| *A61B 5/024* | (2006.01) | |
| *A61B 5/08* | (2006.01) | |

(52) U.S. Cl.
CPC .......... *A61B 5/6844* (2013.01); *A61B 5/0205* (2013.01); *A61B 5/053* (2013.01); *A61B 5/318* (2021.01); *A61B 5/02438* (2013.01); *A61B 5/0816* (2013.01); *A61B 2562/0219* (2013.01)

(58) Field of Classification Search
CPC .......... A61B 2562/0219; A61B 5/0205; A61B 5/024; A61B 5/02438; A61B 5/0402; A61B 5/053; A61B 5/0535; A61B 5/0816; A61B 5/113; A61B 5/6804; A61B 5/6844
See application file for complete search history.

(56) References Cited

U.S. PATENT DOCUMENTS

2007/0100666 A1 *    5/2007    Stivoric .............. A61B 10/0012
                                                                    705/3
2014/0228657 A1 *    8/2014    Palley ................ A61B 5/14551
                                                                    600/324

* cited by examiner

*Primary Examiner* — George Manuel

(57) ABSTRACT

A system, apparatus, and method using multiple complementary sensors for the monitoring and wireless communication of several respiration characteristics—that is badge-size, wearable on the outside of clothing, and non-invasive.

6 Claims, 8 Drawing Sheets

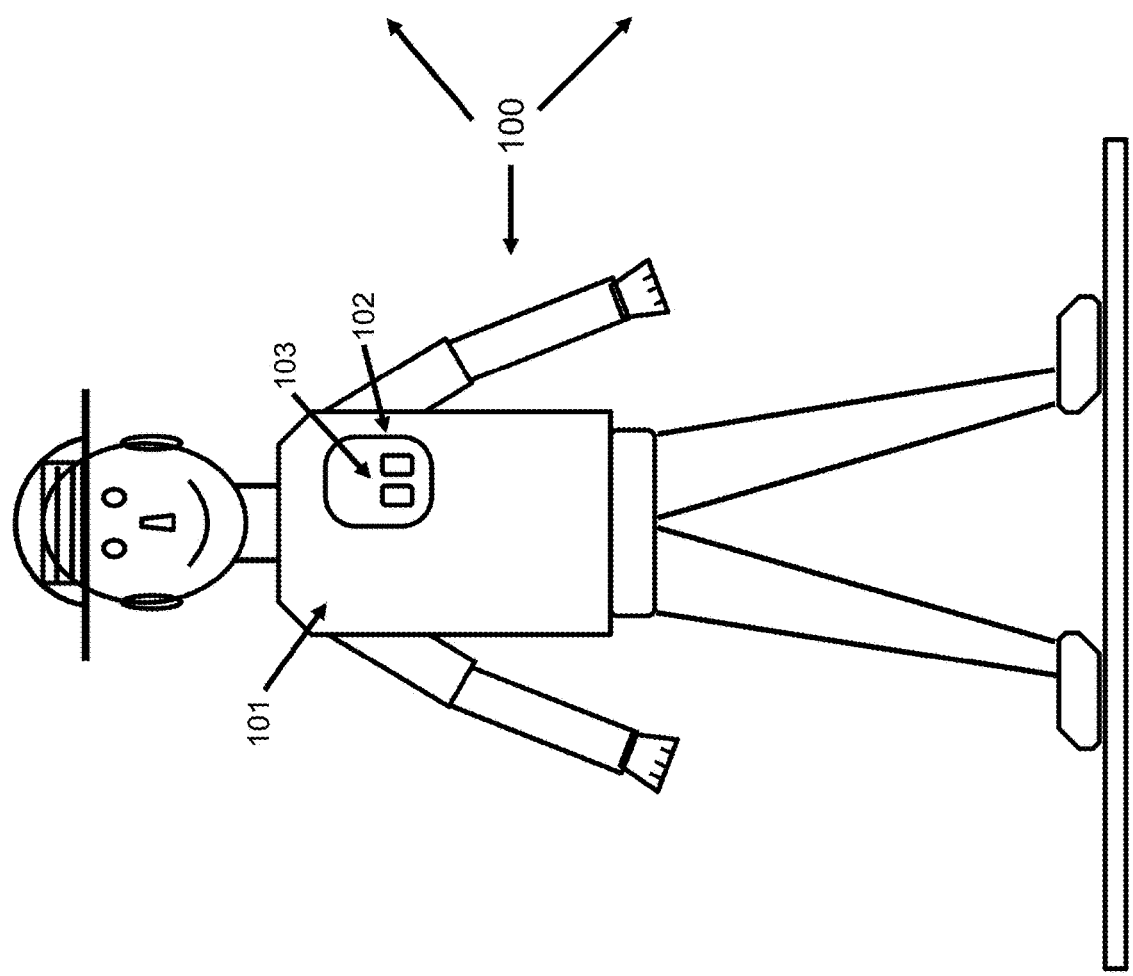
FIGURE 1

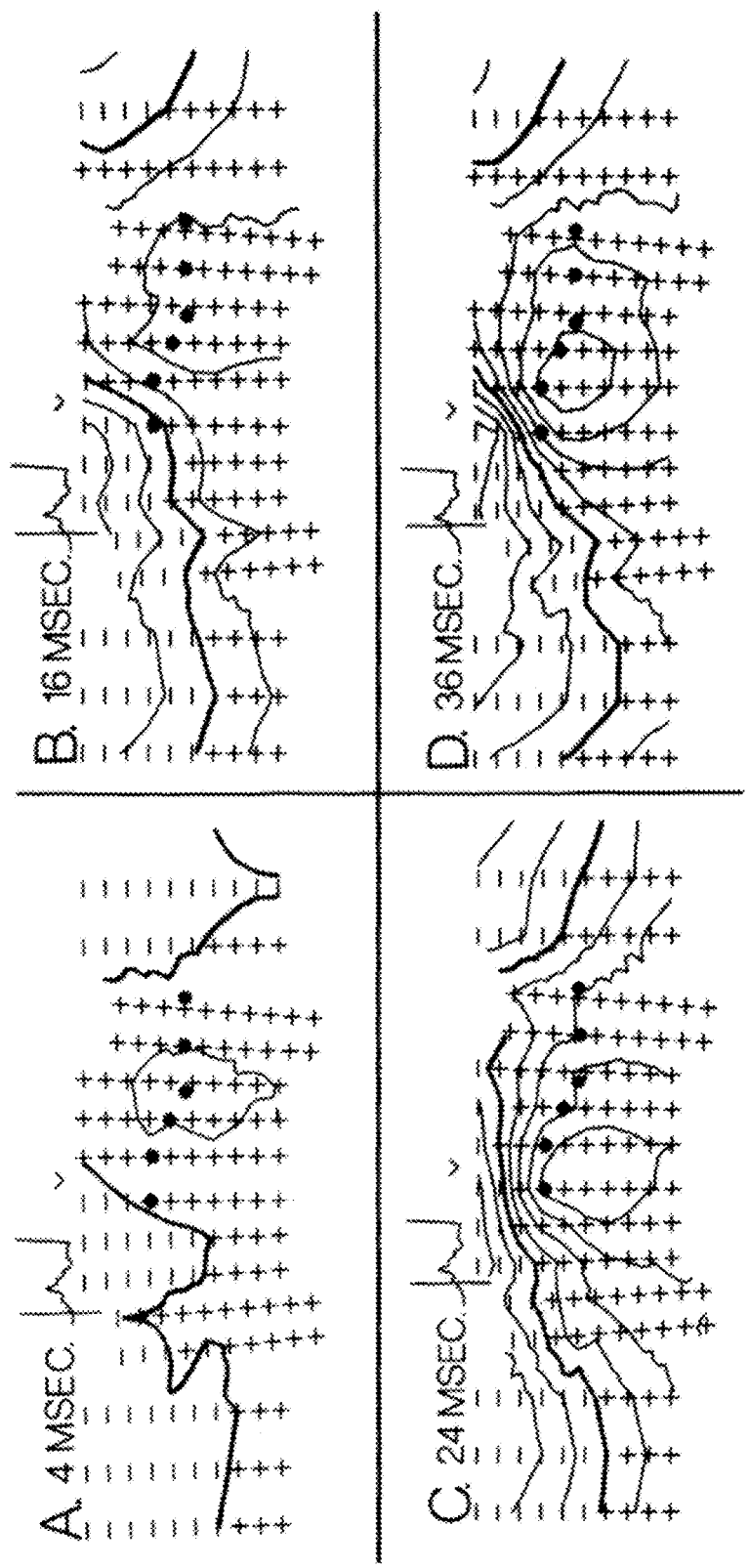
FIGURE 3A (Prior Work)

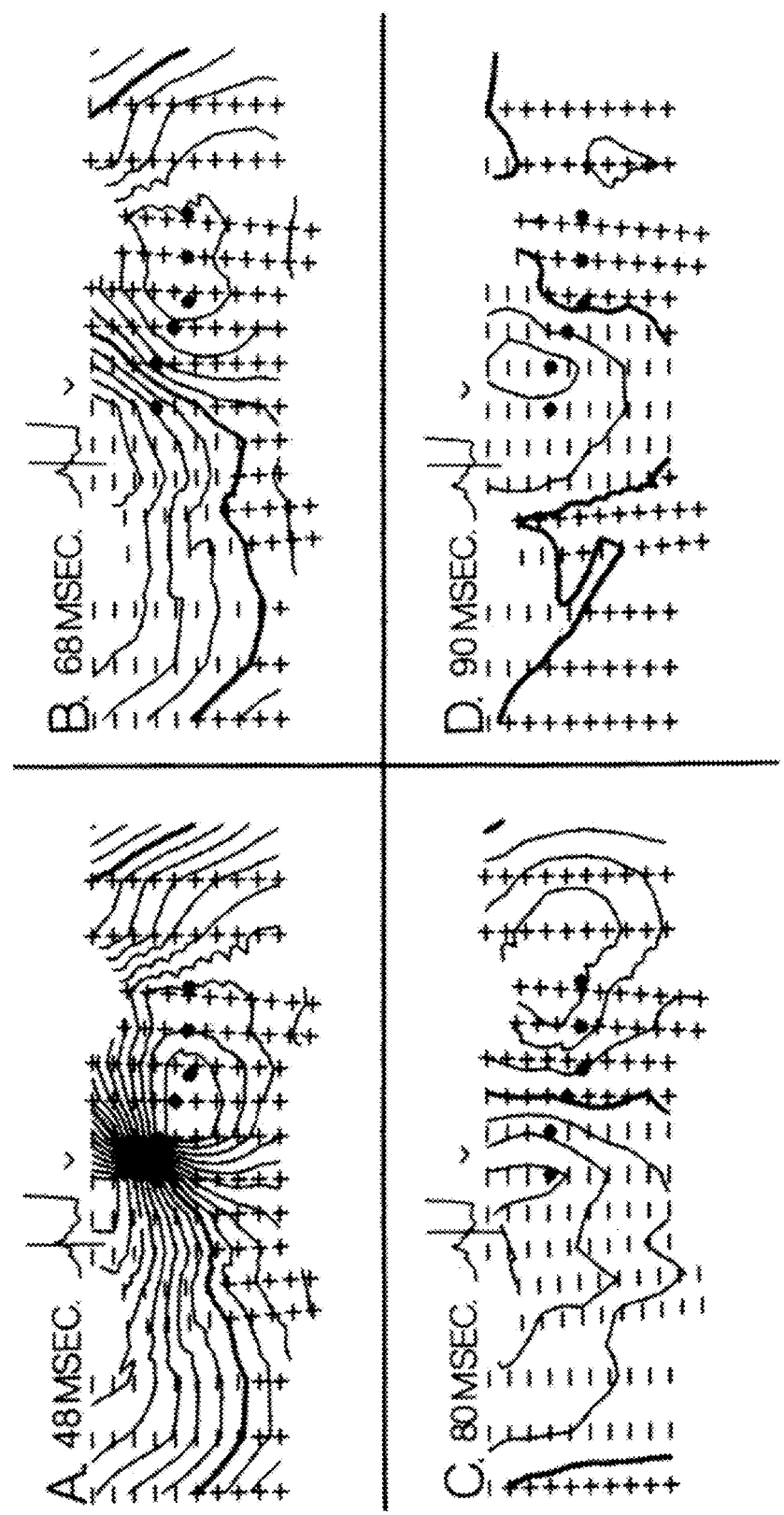

FIGURE 3. Isopotential body surface maps drawn at instants 48 msec (A), 68 msec (B), 80 msec (C) and 90 msec (D) after the onset of the P wave. All conventions and contour intervals are as in figure 2.

From: "Body Surface Distribution of Electrical Potential during Atrial Depolarization and Repolarization" D. M. Mirvis, MD Univ. of Tennessee, "Circulation" 62, No. 1, 1980 (circ.ahajournals.org/content/circulationaha/62/1/167)

FIGURE 3B (Prior Work)

MULTIPLE SENSOR WEARABLE AND PORTABLE NON-INVASIVE RESPIRATION MONITORING INSTRUMENTATION

CROSS-REFERENCE TO RELATED APPLICATION

Priority is claimed under 37 CFR 1.78 and 35 USC 119(e) to U.S. Provisional Application 62/632,907 (XT1802201), filed 20 Feb. 2018, which is incorporated by reference.

TECHNICAL FIELD

This disclosure relates generally to the non-invasive measurement of bodily functions. More specifically, this disclosure relates to the simultaneous use of multiple sensors and circuitry located within a non-intrusive wearable and portable instrument for the reliable detection, characterization, and real time wireless communication of the respiration function. The instrument is safe, convenient to use and maintain, and reliable, regardless of activity level and orientation of the wearer.

BACKGROUND

Apparatus to monitor the breathing of subjects has existed for many years. "Breathing is one of the most obvious signs of human vitality and activity; however, it can also reflect the status of a patient and the progression of an illness. The entire process, from inhalation to the exhalation, is referred to as the breathing or respiration cycle (RC). Respiratory rate indicates the frequency of breathing or the time between two consecutive RCs. Any alterations in the respiratory rate can help predict potentially serious clinical events, such as a cardiac arrest, or it may suggest that a patient be admitted to an intensive-care unit." (Cretikos, M.A.; Bellomo, R.; Hillman, K.; Chen, J.; Finfer, S.; Flabouris, A. Respiratory rate: The neglected vital sign. Med. J. Aust. 2008, 188, 657-659)

It is considered important to monitor the time pattern, volume, and depth of respiration of a variety of subjects, such as infants, athletes, truck drivers, soldiers in the field, as well as those already known to suffer from dangerous medical conditions. It has also been demonstrated that detailed knowledge of breathing characteristics supports the ability to diagnose disease conditions. Such knowledge can be used to recommend therapeutic procedures to prevent or forestall further permanent medical damage and/or death. Moreover, as respiration monitoring products become more convenient and economical, it will be used routinely, including by those who are ill but are unaware of it.

Historically, respiratory measurements have not only lacked the cost requirements and convenience to encourage every-day and every-night out-of-clinic use, but they have been unavailable to infants and children, who do not tolerate invasive or intrusive equipment. People in general do not choose intrusive and/or inconvenient monitoring systems for themselves or loved ones, unless there is already a strong indication of adverse medical conditions.

Examples of intrusive and/or invasive respiration measurement systems include belts with strain sensors, nasal air flow rate and/or temperature sensing during the breathing cycle, and processed electrocardiogram data. Examples of non-intrusive respiration measurement systems include photographic methods and ultra-wideband pulse radar. These latter systems are neither portable nor wearable. Clearly there is a need for a respiration measurement instrument system that is wearable, non-invasive, non-intrusive, and portable.

BRIEF SUMMARY

This Brief Summary is provided as a general introduction to the Disclosure provided by the Detailed Description and Figures, summarizing some aspects of the disclosed invention. It is not a detailed overview of the Disclosure and should not be interpreted as identifying key elements of the invention, or otherwise characterizing the scope of the invention disclosed in this Patent Document.

The portable, wearable, and non-intrusive/non-invasive respiration monitoring system described in the instant disclosure is contained in a badge-sized, light, and safe enclosure that easily attaches to the outside of inner clothing, i.e. makes no contact with the skin. All sensors, measurement circuitry, power source and management, signal processing, data storage, and wireless communication circuitry are contained within the enclosure.

The present example embodiment includes three sensors, having complementary uses to detect and characterize breathing, depending upon the position and activity of the wearer, as well as the relative motion of the wearer and clothing. The detected and processed signals are of sufficient quality to monitor several critical aspects of respiration: breathing rate, depth, volume, and pattern. These sensors draw extremely low power and are intrinsically safe. They induce no electric currents within the body and make use of naturally occurring physical effects within the skin. In addition to said principal function, these sensors could be used to detect and communicate, whether or not said monitoring system is or is not attached to a subject.

One sensor is a three-axis accelerometer that operates successfully during periods when the clothing to which the monitoring system enclosure is attached is very thin and tight against the wearer/subject's body. A second sensor measures the capacitance between its electrodes and the body. It is useful when the monitor is up to several centimeters from the body, such as when attached to the outside of a diaper. The third sensor operates efficiently when the clothing is separated from the skin within the range of 1 to 10 centimeters, such as on the outside of loose, hanging clothing. Its set of electrodes develops electric potential differences that are caused by naturally occurring potential differences on the skin, through the intermediary of the electric field created by the latter.

Other aspects, features and advantages of the invention will be apparent to those skilled in the art from the following Disclosure.

BRIEF DESCRIPTION OF DRAWINGS

For a more complete understanding of this disclosure and its features, reference is now made to the following description, taken in conjunction with the accompanying drawings, in which:

FIG. 1 illustrates a basic wearable multiple sensor respiration Monitor on three subjects.

FIG. 3A, 3B displays prior work that established, by application of ECG probes, potential gradients on the skin surface.

DETAILED DESCRIPTION

The various figures, discussed below, and the various embodiments used to describe the principles of the present invention in this patent document are by way of illustration only and should not be construed in any way to limit the scope of the invention. Those skilled in the art will understand that the principles of the invention may be implemented in any type of suitably arranged device or system.

In general, this disclosure provides the description of a novel, multiple complementary sensor contained in a non-intrusive, non-invasive portable and wearable system to monitor respiration and its detailed characteristics.

Depending on the implementation, this technique can provide significant benefits in a range of fields, such as detection and monitoring of unfavorable health conditions indicated by specific respiration rates, patterns, volume, and depth.

FIG. 1 illustrates a basic wearable multiple sensor respiration Monitor on three subjects 100. The subject on the left is wearing an undergarment 101, with a Monitor assembly 102 that contains a multiplicity of sensors used for breathing and other bodily functions. One said sensor, 103, is designed to register the existence of an electric field having some component in the horizontal direction by creating an electric potential difference between the illustrated electrodes. Sensor 103 and the remaining sensors (not shown) are connected to measurement and processing circuitry as well as wireless communications circuitry. Monitor 102 is smaller, relative to the size of the subject, than the one shown in the figure. Not shown in the figure are any over-garments that cover the undergarment 101 and Monitor 102, allowing the latter to be comfortable and unobtrusive. Monitor Assembly 102 could be attached to clothing on many parts of the body, including, as examples, to the outside of a diaper or sleepwear, as shown for the remaining two subjects in the figure.

Figure 2B:
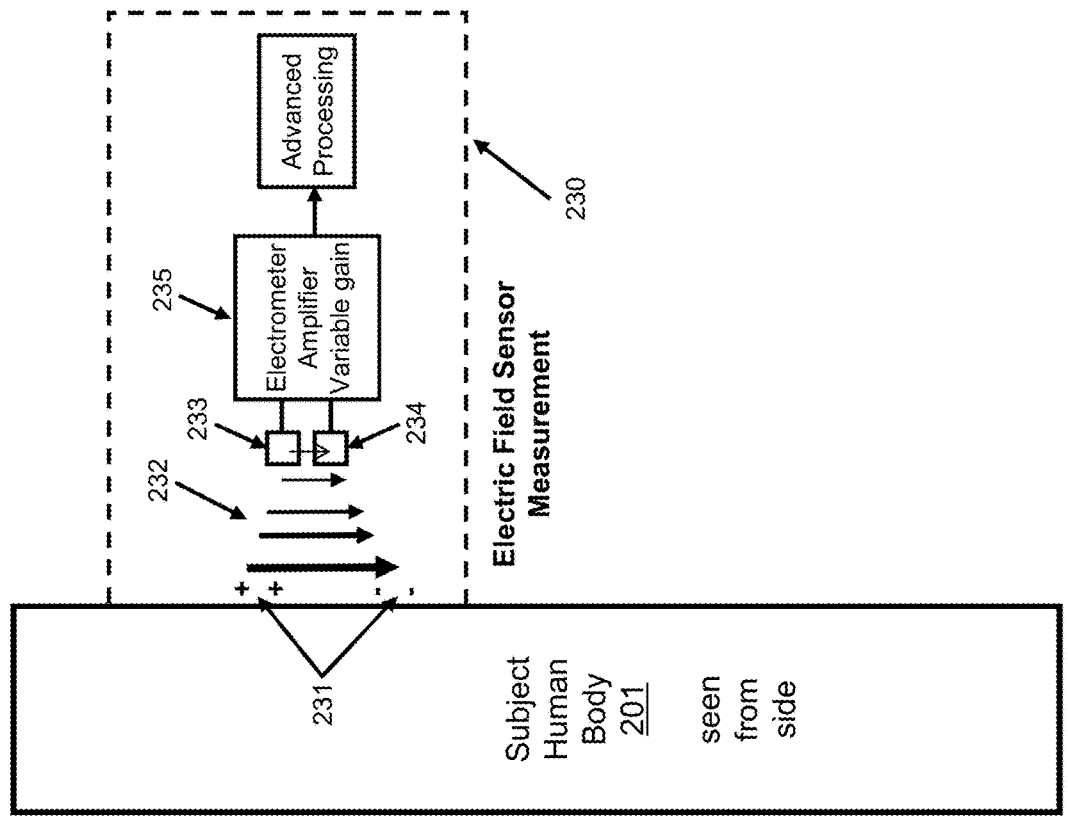
FIG. 2 shows a block diagram of the Respiration Monitor attached to a Human Body.
Figure 2A:
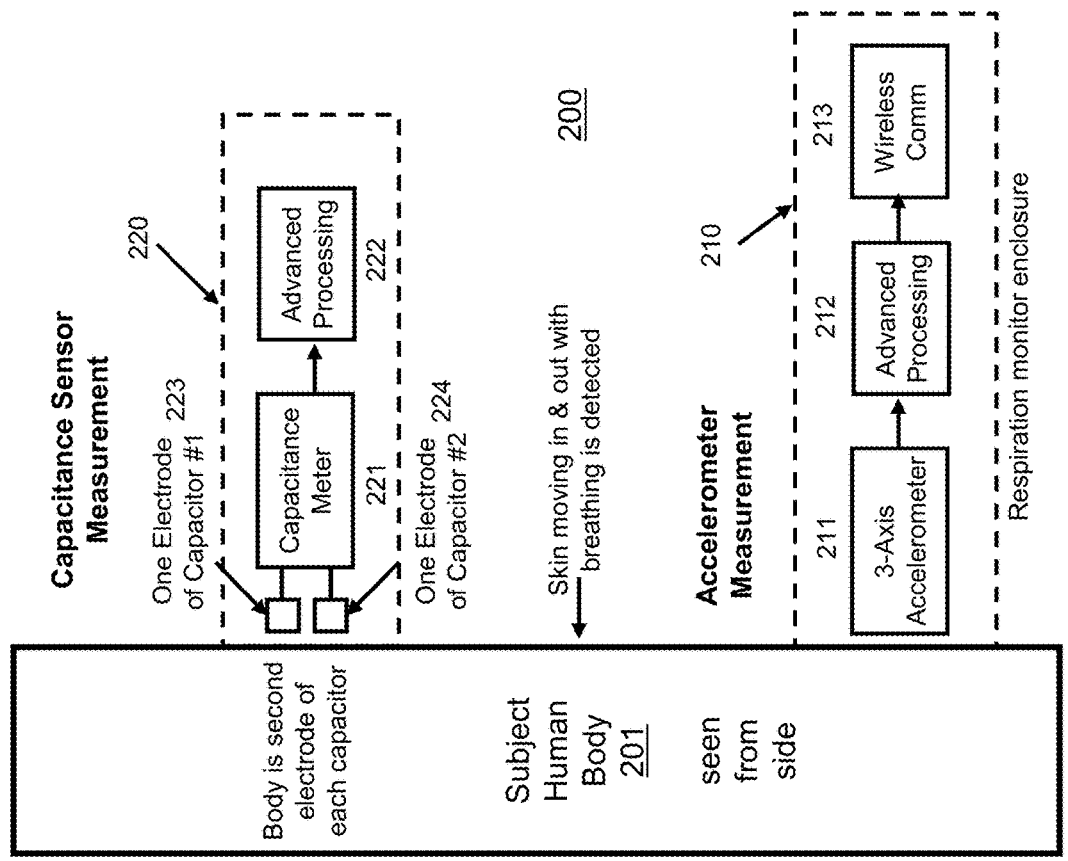

FIG. 2 shows a block diagram of the Respiration Monitor 200 attached to Human Body 201. FIG. 2A illustrates functioning of said accelerometer measurement block 210 and capacitance measurement block 220, and FIG. 2B illustrates functioning of said electric field sensor block 230. Not shown is that all three sensors and processing circuitry are contained within the Respiration Monitor 200 Enclosure, and that the Wireless Communication module 213 services everything in the Monitor.

The 3-axis accelerometer sensor 211 detects breathing when the Respiration Monitor Enclosure is in close contact with the body surface, including on the outside of thin clothing. The raw data from the accelerometer sensor 211 is refined by advanced processing block 212, which includes filtering and other processing, such as artificial intelligence circuitry.

If the Respiration Monitor is 200 separated from the body surface but by not more than about 5 centimeters, the capacitance measurement block 220 detects breathing. Capacitor #1 223 electrodes include the one shown in the Figure and the body surface. Correspondingly, Capacitor #2 224 electrodes include the one shown in the Figure and the body surface. The capacitance meter 221 sees the two capacitors 223, 224 as a series circuit. The relative positions of the body surface and Monitor 200 modulate the capacitance seen by the meter 221. The advanced processing circuitry 222 distinguishes the breathing curve from any miscellaneous motion of loose clothing. This capacitive measurement block 220 operates in both low and high humidity environments.

When the Subject is active and wearing loose clothing, separation of the body surface and Respiration Monitor may exceed several centimeters. In this case, the Electric Field measurement block 230—depicted in FIG. 2B—which operates with a separation of up to about 10 centimeters, is utilized. It has been shown that electrical potential gradients 231 exist on the skin, which are correlated with aspects of the breathing cycle, such as depth. Potential gradients 231 on the skin surface cause electric fields 232 that extend beyond the skin surface. If the there is a finite component of the electric field 232 vector in the direction along the axis of the electrode assembly 233, 234, a potential (voltage) exists between these electrodes. Said voltage is detected with an extremely high impedance (electrometer) amplifier 235 that includes an automatic gain control feature to handle a large range of signal levels.

FIG. 3A, 3B displays prior work that established by application of ECG probes the existence, magnitudes, and spatial and time patterns of said potential gradients on the skin surface. The captions therein adequately describe the measurement results and are not repeated in the instant Specification text.

Figure 4:
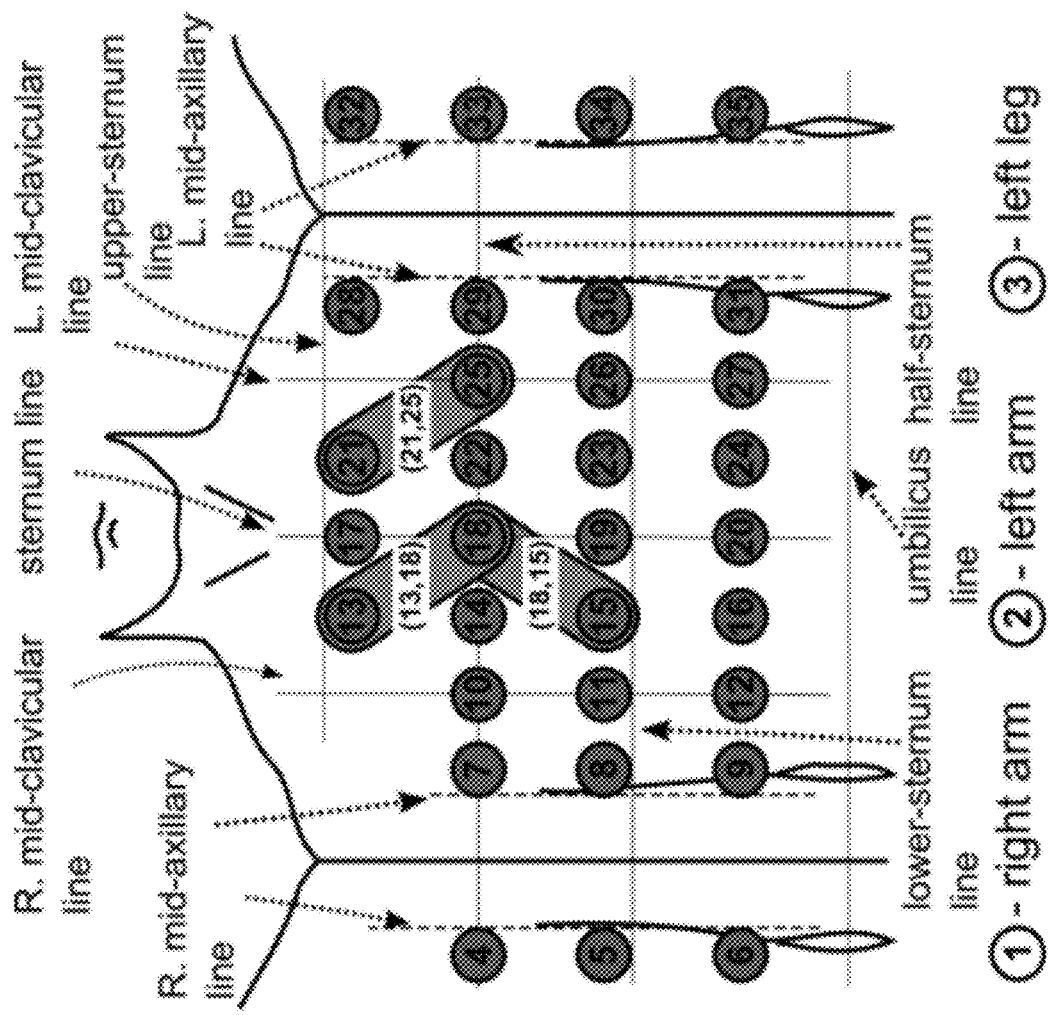
FIG. 4 displays prior work showing that body surface potential variations can be used to derive rate and other features of respiration.

FIG. 4 displays prior work showing that body surface potential variations, measured by a pair of ECG-type electrodes, can be used to derive rate and other features of respiration. A 37-lead ECG system was used to identify the most favorable proximal location pairs to probe.

Figure 5:
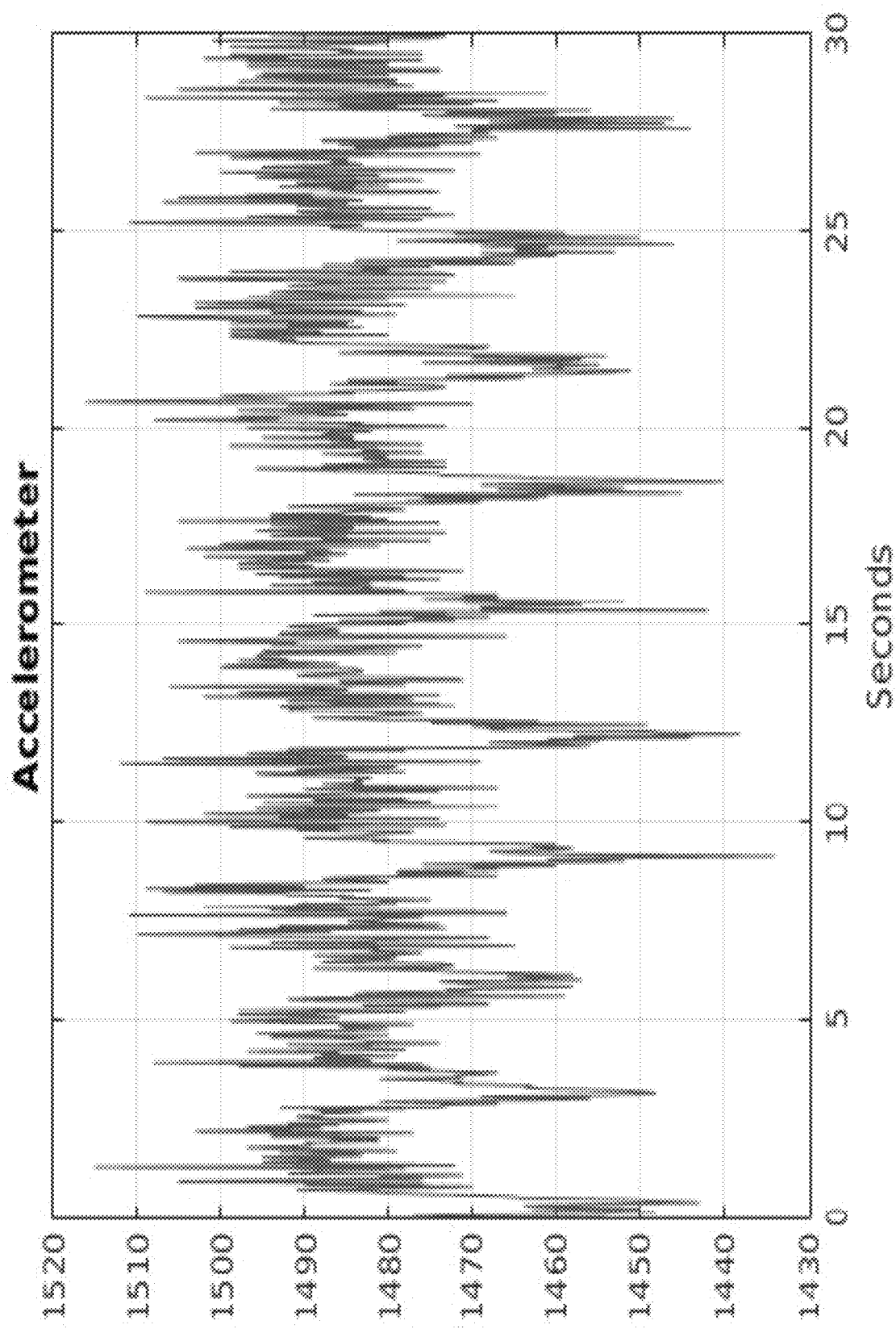
FIG. 5 shows measured respiration data from an accelerometer contained in a wearable monitor designed by the inventor.
Figure 6:
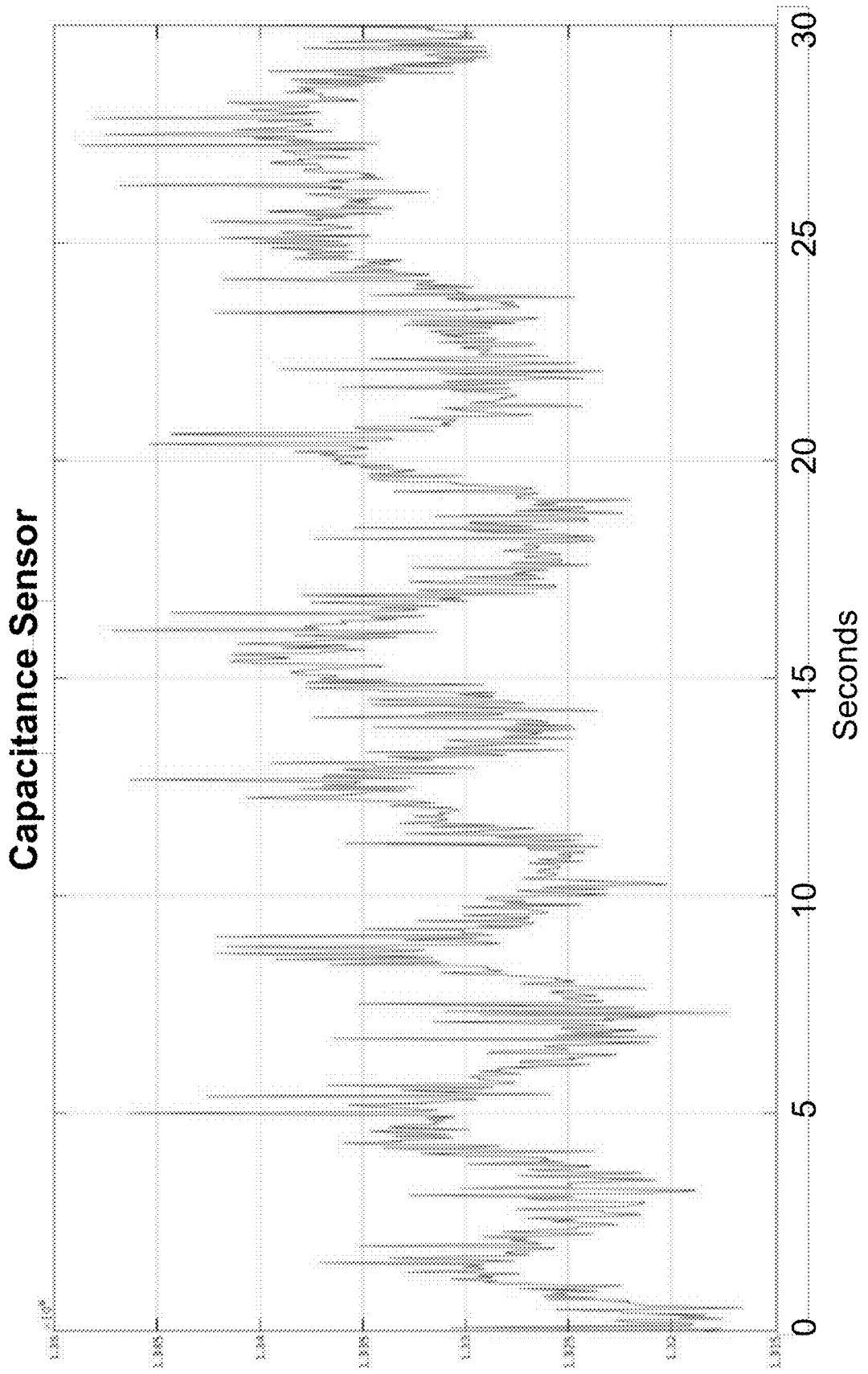
FIG. 6 shows measured respiration data from a capacitance sensor contained in a wearable monitor designed by the inventor.
Figure 7:
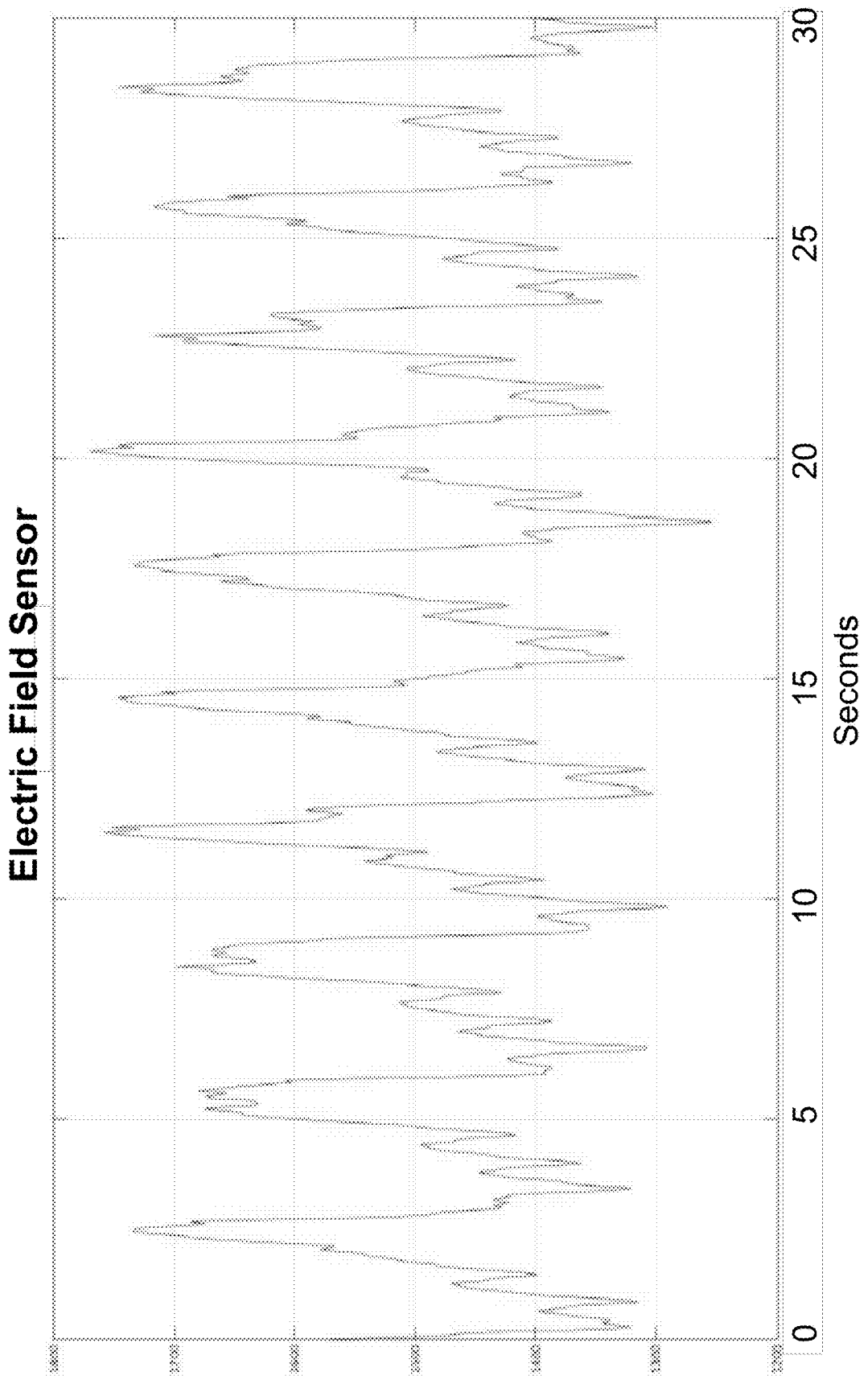
FIG. 7 shows measured respiration data from an electric field sensor contained in a wearable monitor designed by the inventor.

FIGS. 5, 6, and 7 show measured respiration data from the accelerometer measurement module 210, capacitance measurement module 220, and electric field measurement module 230 respectively. Said data was acquired from said measurement modules as part of the complete portable, wearable and non-intrusive/non-invasive respiration monitoring system 200 as described in the instant disclosure. The data is raw, prior to the extensive cleanup processing contained with said monitoring system. The linear vertical scales shown are arbitrary. Hidden in the data may be pulse rate and/or ECG information, which may be recoverable using various additional processing methods.

The details provided in the instant specification describe particular implementations of systems for portable, wearable and non-intrusive/non-invasive respiration monitoring. Other embodiments could be implemented in any other suitable manner.

It may be advantageous to set forth definitions of certain words and phrases used throughout this patent document. The term "couple" and its derivatives refer to any direct or indirect communication between two or more elements, whether or not those elements are in physical contact with one another. The terms "transmit," "receive," and "communicate," as well as derivatives thereof, encompass both direct and indirect communication. The terms "include" and "comprise," as well as derivatives thereof, mean inclusion without limitation. The term "or" is inclusive, meaning and/or. The phrases "associated with" and "associated therewith," as well as derivatives thereof, may mean to include, be included within, interconnect with, contain, be contained within, connect to or with, couple to or with, be communicable with, cooperate with, interleave, juxtapose, be proximate to, be bound to or with, have, have a property of, have a relationship to or with, or the like.

While this disclosure has described certain embodiments and generally associated methods, alterations and permutations of these embodiments and methods will be apparent to those skilled in the art. Accordingly, the above description of example embodiments does not define or constrain this disclosure. Other changes, substitutions, and alterations are also possible without departing from the spirit and scope of this disclosure, as defined by the following claims.

What is claimed is:

1. A method to monitor respiration using an unobtrusive badge-size apparatus comprising:
   an accelerometer sensor whose output data is used to calculate a periodic expansion and contraction of a body surface during respiration
      when said apparatus is either in contact with the skin or on the outside of thin, tight clothing;
   a capacitance sensor consisting of two series-connected capacitors, where a first conductor of each capacitor is located within said apparatus, and the body surface forms a second conductor of each capacitor and provides said series connection, where
      said apparatus is attached to the outside of clothing whose separation from the body varies between zero and about 3 centimeters,
      the periodic expansion and contraction of the body surface during respiration varies a capacitance of the capacitance sensor; and
   an electrometer or other electric field sensing instrument that measures electric fields produced by electric charge gradients on the body surface that vary predictably during the respiration cycle,
      where said electric fields extend greater than about 3 centimeters from the body surface,
      thereby allowing said apparatus to be mounted on very loose clothing;
   whereby said apparatus containing an array of complementary sensors monitors respiration rate and depth as a function of time, all while attached to any layer of clothing.

2. The method of claim 1, but also used to monitor pulse rate, which-can also be detected via motions of the body surface.

3. The method of claim 1, but also includes, through its monitoring of respiration, the ability to detect whether or not the apparatus is located on a wearer/subject, regardless of how close the apparatus is to the wearer/subject.

4. A system to monitor and report respiration using an unobtrusive badge-size apparatus comprising:
   an accelerometer sensor whose output data is used to calculate a periodic expansion and contraction of a body surface during respiration
      when said apparatus is either in contact with the skin or on the outside of thin, tight clothing;
   a capacitance sensor consisting of two series-connected capacitors, where a first conductor of each capacitor is located within said apparatus, and the body surface forms a second conductor of each capacitor and provides said series connection, where
      said apparatus is attached to the outside of clothing whose separation from the body varies between zero and about 3 centimeters,
      the periodic expansion and contraction of the body surface during respiration varies a capacitance of the capacitance sensor;
   an electrometer or other electric field sensing instrument that measures electric fields produced by electric charge gradients on the body surface that vary predictably during the respiration cycle,
      where said electric fields extend greater than about 3 centimeters from the body surface,
      thereby allowing said apparatus to be mounted on very loose clothing;
   a signal processing and control module to condition and interpret said sensor data and format it for transmission, and
   a wireless communication module to send said respiration data for further analysis and display;
   whereby said apparatus containing an array of complementary sensors monitors and reports respiration rate and depth as a function of time, all while attached to any layer of clothing.

5. The system of claim 4, but also used to monitor pulse rate, which-can also be detected via motions of the body surface.

6. The system of claim 4, but also includes, through its monitoring of respiration, the ability to detect whether or not the apparatus is located on a wearer/subject, regardless of how close the apparatus is to the wearer/subject.

* * * * *